United States Patent [19]

Faustini et al.

[11] Patent Number: 4,808,578
[45] Date of Patent: Feb. 28, 1989

[54] 6-ALKYLIDENE 10 β-ALKYNYLESTRENE DERIVATIVES AND PHARMACEUTICAL METHODS FOR THEIR USE

[75] Inventors: Franco Faustini; Enrico di Salle; Vittoria Villa; Paolo Lombardi, all of Milan, Italy

[73] Assignee: Farmitalia Carlo Erba S. R. L., Milan, Italy

[21] Appl. No.: 941,348

[22] Filed: Dec. 15, 1986

[30] Foreign Application Priority Data

Dec. 24, 1985 [GB] United Kingdom ............... 8531747

[51] Int. Cl.$^4$ .......................... A61K 31/56; C07J 1/00
[52] U.S. Cl. ................................. 514/177; 260/397.3
[58] Field of Search ...................... 514/177; 260/397.3

[56] References Cited

U.S. PATENT DOCUMENTS

| 2,744,120 | 5/1956 | Fried et al. | 260/343.2 |
| 4,289,762 | 9/1981 | Metcalf et al. | 424/242 |
| 4,322,416 | 3/1982 | Metcalf et al. | 514/177 |
| 4,446,071 | 5/1984 | Varna | 260/397.3 |

FOREIGN PATENT DOCUMENTS

| 0161492 | 11/1985 | European Pat. Off. . |
| 1042291 | 11/1961 | United Kingdom . |
| 2078749 | 1/1982 | United Kingdom . |
| 2100601 | 1/1983 | United Kingdom . |

Primary Examiner—Leonard Schenkman
Assistant Examiner—Joseph A. Lipovsky
Attorney, Agent, or Firm—Armstrong, Nikaido, Marmelstein & Kubovcik

[57] ABSTRACT

The invention relates to 6-substituted 10β-alkynylestrene derivatives wherein the 6 substituent is amino, azido, halogen or an alkylidene group and to corresponding 6,7-dihalo analogs.

The invention provides also a process for the preparation of the above compounds and pharmaceutical compositions containing same.

The compounds of the invention are useful aromatase inhibitors and can be used, e.g., in the treatment of hormone-dependent tumors and prostatic hyperplasia.

9 Claims, No Drawings

6-ALKYLIDENE 10 β-ALKYNYLESTRENE DERIVATIVES AND PHARMACEUTICAL METHODS FOR THEIR USE

DESCRIPTION

The present invention relates to novel 6-substituted 10β-alkynylestr-4-ene derivatives, to a process for their preparation, to pharmaceutical compositions containing them, and to the use of said compounds for the treatment of hormone-dependent cancers in mammals. Basic and clinical data indicate that aromatized metabolites of androgens, i.e. the estrogens, are the hormones involved in the pathogenic cellular changes associated with the growth of some hormone-dependent cancers, such as breast, endometrial, ovarian and pancreatic carcinomas.

Estrogens are also involved in the pathogenesis of benign prostatic hyperplasia.

Endogenous estrogens are ultimately formed from either androstenedione or testosterone as immediate precursors. The reaction of central importance is the aromatization of the steroidic ring A, which is performed by the enzyme aromatase. As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumors.

Known steroidal substances which have been reported to be endowed with an aromatase-inhibiting action are, for example, testololactone [U.S. Pat. No. 2,744,120], 4-hydroxy-androst-4-ene-3,17-dione and esters thereof [see, for example, U.S. Pat. No. 4,235,893], 10-(1,2-propadienyl)-estr-4-ene-3,17-dione [U.S. Pat. No. 4,289,762], 10-(2-propynyl)-estr-4-ene-3,17-dione [J. Am. Chem. Soc., 103, 3221 (1981) and U.S. Pat. No. 4,322,416], 19-thioandrostene derivatives (European patent application No. 100566), androsta-4,6-diene-3,17-dione and androsta-1,4,6-triene-3,17-dione [G.B. patent application No. 2,100,601A], and androsta-1,4-diene-3,17-dione [Cancer Res. (Suppl.) 42, 3327 (1982)].

The novel compounds of the present invention, besides exhibiting a potent in vitro inhibition of the aromatase, are endowed with a superior in vivo potency by virtue of their better metabolic stability when compared to the compounds of the previous art.

The present invention provides compounds having the following general formula (I)

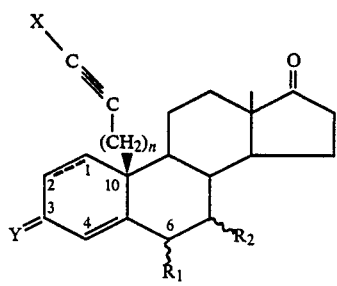

(I)

wherein
X is hydrogen, $C_1$–$C_4$ alkyl or halogen;
n is zero, 1 or 2;
Y is an oxo group or a methylene group; the symbol $\doteq$ indicates a single bond or a double bond;
$R_1$ is halogen, azido or a group

wherein each of $R_3$ and $R_4$ is, independently, hydrogen or $C_1$–$C_4$ alkyl, or $R_1$ may be divalent and is a $C_1$–$C_6$ alkylidene group; and
$R_2$ is hydrogen or, when $R_1$ is halogen, $R_2$ may also be the same halogen as $R_1$.

Object of the invention are also the pharmaceutically acceptable salts of the compounds of formula (I) containing a salifiable group.

In the formulae of this specification a dotted line (ııııııı) indicates a substituent in the α-configuration, i.e. below the plane of the ring; a wedged line (──■) indicates a substituent in the β-configuration, i.e. above the plane of the ring; and a wavy line (∼) indicates that a substituent may be in the α-configuration or in the β-configuration or both. Consequently, where a formula has a substituent with a wavy line bond, the formula may represent a compound having the substituent solely in the α-configuration or solely in the β-configuration, or the formula may represent a mixture of both compounds having the substituent in the α-configuration and compounds having the substituent in the β-configuration.

It is intended that the present invention includes all the possible isomers of formula (I), both separately and in mixture.

In this specification the alkyl and alkylidene groups may be branched or straight chain.

A $C_1$–$C_4$ alkyl group is, preferably, methyl, ethyl, n-propyl or tert.butyl.

A halogen atom may be iodine, bromine, chlorine or fluorine. A $C_1$–$C_6$ alkylidene group is, preferably, $C_1$–$C_4$ alkylidene, in particular, e.g., methylene($CH_2$=), ethylidene($CH_3$—CH=) or n-propylidene($CH_3$—$CH_2$—CH=), most preferably methylene. When X is $C_1$–$C_4$ alkyl, methyl and ethyl are preferred, particularly methyl; when X is halogen, iodine and bromine are preferred.

When $R_1$ is a group

preferably $R_3$ and $R_4$ are both hydrogen, or one of them is hydrogen and the other is $C_1$–$C_4$ alkyl, in particular methyl or ethyl, particularly preferred value of

being —$NH_2$.

When $R_1$ is $C_1$–$C_6$ alkylidene, methylene, i.e. =$CH_2$, is particularly preferred.

When $R_1$ is halogen, the halogen is, preferably, bromine or iodine, and the same is for $R_2$ when it is halogen too. Pharmaceutically acceptable salts of the compounds of formula (I) containing a salifiable group are those of the compounds of formula (I) where $R_1$ is a group

wherein $R_3$ and $R_4$ are as defined above, with pharmaceutically acceptable acids, both inorganic acids, such as, for example, hydrochloric, nitric, sulfuric or phosphoric acid, and organic acids such as, e.g., citric, fumaric, maleic, malic, ascorbic, tartaric, benzoic, acetic, phenylacetic, cyclohexylacetic, 3-cyclohexylpropionic, methanesulfonic, ethanesulfonic, benzenesulfonic, p-toluenesulfonic or p-nitrobenzenesulfonic acid. Also the quaternary ammonium salts and hydroxides of the compounds of formula (I) containing a group

are within the scope of the invention: they are, for instance, quaternary alkyl, e.g., methyl, ethyl or cetyl, ammonium salts, e.g. iodides, bromides or chlorides, or hydroxides.

Preferably in the above formula (I) X is hydrogen or halogen, i.e. iodine, bromine, chlorine or fluorine, especially iodine or bromine; Y is an oxo group; $R_1$ is halogen, preferably bromine or iodine, azido or a group

as defined above, especially a group $-NH_2$; $R_2$ is hydrogen or, when $R_1$ is halogen, $R_2$ is the same halogen as $R_1$.

A preferred class of compounds under this invention are the compounds of formula (I) wherein X is hydrogen, $C_1$–$C_4$ alkyl or halogen; n is zero, 1 or 2; Y is an oxo group; the symbol $\equiv\equiv\equiv$ represents a single or a double bond; $R_1$ is a group $C_1$–$C_6$ alkylidene, or azido, or a group

wherein $R_3$ and $R_4$ are as defined above, and $R_2$ is hydrogen, and the pharmaceutically acceptable salts of those compounds containing a salifiable group.

In the above preferred class particularly preferred X values are hydrogen and halogen, i.e. iodine, bromine, chlorine or fluorine, in particular iodine or bromine; a particularly preferred $C_1$–$C_6$ alkylidene group is methylene; a particularly preferred value of

is $-NH_2$. Another preferred class of compounds under the invention are the compounds of formula (I) wherein X is hydrogen, $C_1$–$C_4$ alkyl or halogen; n is zero, 1 or 2; is an oxo group; the symbol $\equiv\equiv\equiv$ represents a single or a double bond; $R_1$ is halogen and $R_2$ is hydrogen or the same halogen as $R_1$.

In the above preferred class, particularly preferred X values are hydrogen and iodine; particularly preferred n value is 1; $R_1$ is, preferably, bromine or iodine and $R_2$ is, preferably, hydrogen, bromine or iodine.

Examples of specific compounds under the invention are:

10β-(2-propynyl)-6-methylenestra-1,4-diene-3,17-dione;
10β-(3-iodo-2-propynyl)-6-methylenestra-1,4-diene-3,17-dione;
10β-(3-bromo-2-propynyl)-6-methylenestra-1,4-diene-3,17-dione;
10β-(3-chloro-2-propynyl)-6-methylenestra-1,4-diene-3,17-dione;
10β-(3-fluoro-2-propynyl)-6-methylenestra-1,4-diene-3,17-dione;
10β-(2-propynyl)-6α-azidoestra-1,4-diene-3,17-dione;
10β-(3-iodo-2propynyl)-6α-azidoestra-1,4-diene-3,17-dione;
10β-(3-bromo-2propynyl)-6α-azidoestra-1,4-diene-3,17-dione;
10β-(3-chloro-2-propynyl)-6α-azidoestra-1,4-diene-3,17-dione;
10β-(3-fluoro-2-propynyl)-6α-azidoestra-1,4-diene-3,17-dione;
10β-(2-propynyl)-6-methylenestr-4-ene-3,17-dione;
10β-(3-iodo-2propynyl)-6-methylenestr-4-ene-3,17-dione;
10β-(3-bromo-2-propynyl)-6-methylenestr-4-ene-3,17-dione;
10β-(3-chloro-2-propynyl)-6-methylenestr-4-ene-3,17-dione;
10β-(3-fluoro-2-propynyl)-6-methylenestr-4-ene-3,17-dione;
10β-(2-propynyl)-6α-azidoestr-4-ene-3,17-dione;
10β-(3-iodo-2-propynyl)-6α-azidoestr-4-ene-3,17-dione;
10β-(3-bromo-2-propynyl)-6α-azidoestr-4-ene-3,17-dione;
10β-(3-chloro-2-propynyl)-6α-azidoestr-4-ene-3,17-dione;
10β-(3-fluoro-2-propynyl)-6α-azidoestr-4-ene-3,17-dione;
10β-(2-propynyl)-6β-bromoestra-1,4-diene-3,17-dione;
10β-(3-iodo-2propynyl)-6β-bromoestra-1,4-diene-3,17-dione;
10β-(3-bromo-2-propynyl)-6β-bromoestra-1,4-diene-3,17-dione;
10β-(3-chloro-2propynyl)-6β-bromoestra-1,4-diene-3,17-dione;
10β-(3-fluoro-2-propynyl)-6β-bromoestra-1,4-diene-3,17-dione;
10β-(2-propynyl)-6β-bromoestr-4-ene-3,17-dione;
10β-(3-iodo-2-propynyl)-6β-bromoestr-4-ene-3,17-dione;
10β-(3-bromo-2propynyl)-6β-bromoestr-4-ene-3,17-dione;

10β-(3-chloro-2-propynyl)-6β-bromoestr-4-ene-3,17-dione;
10β-(3-fluoro-2-propynyl)-6β-bromoestr-4-ene-3,17-dione;
10β-(2-propynyl)-6α-aminoestra-1,4-diene-3,17-dione;
10β-(3-iodo-2-propynyl)-6α-aminoestra-1,4-diene-3,17-dione;
10β-(3-bromo-2propynyl)-6α-aminoestra-1,4-diene-3,17-dione;
10β-(3-chloro-2-propynyl)-6α-aminoestra-1,4-diene-3,17-dione;
10β-(3-fluoro-2propynyl)-6α-aminoestra-1,4-diene-3,17-dione;
10β-(2-propynyl)-6α-aminoestr-4-ene-3,17-dione;
10β-(3-iodo-2-propynyl)-6α-aminoestr-4-ene-3,17-dione;
10β-(3-bromo-2-propynyl)-6α-aminoestr-4-ene-3,17-dione;
10β-(3-chloro-2-propynyl)-6α-aminoestr-4-ene-3,17-dione;
10β-(3-fluoro-2-propynyl)-6α-aminoestr-4-ene-3,17-dione;
10β-(2-propynyl)-6β,7α-dibromoestra-1,4-diene-3,17-dione;
10β-(3-iodo-2-propynyl)-6β,7α-dibromoestra-1,4-diene-3,17-dione;
10β-(3-bromo-2-propynyl)-6β,7α-dibromoestra-1,4-diene-3,17-dione;
10β-(3-chloro-2-propynyl)-6β,7α-dibromoestra-1,4-diene-3,17-dione;
10β-(3-fluoro-2-propynyl)-6β,7α-dibromoestera-1,4-diene-3,17-dione;
10β-(2-propynyl)-6β,7α-dibromoestr-4-ene-3,17-dione;
10β-(3-iodo-2-propynyl)-6β,7α-dibromoestr-4-ene-3,17-dione;
10β-(3-bromo-2-propynyl)-6β,7α-dibromoestr-4-ene-3,17-dione;
10β-(3-chloro-2-propynyl)-6β,7α-dibromoestr-4-ene-3,17-dione;
10β-(3-fluoro-2propynyl)-6β,7α-dibromoestr-4-ene-3,17-dione, and, when appropriate, the pharmaceutically acceptable salts thereof.

The compounds of the invention may be prepared by a process comprising (A) reacting a compound of formula (II)

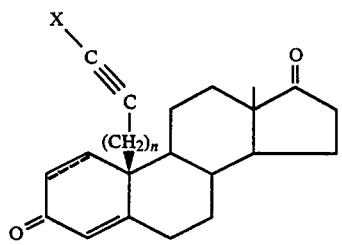

(II)

wherein
n and X are as defined above, with a Vilsmeier reagent, so obtaining a compound of formula (I) wherein n and X are as defined above, Y is an oxo group, === is a single bond, $R_2$ is hydrogen and $R_1$ is a $C_1$–$C_6$ alkylidene group; or (B) halogenating a compound of formula (IIa)

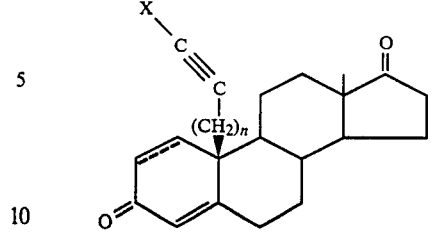

(IIa)

wherein
n and X are as defined above and === is a single or double bond, so obtaining a compound of formula (I) wherein n and X are as defined above, === is a single or double bond, Y is an oxo group, $R_2$ is hydrogen and $R_1$ is halogen; or (C) halogenating a compound of formula (III)

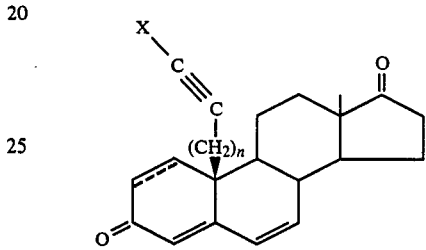

(III)

wherein
n and X are as defined above and === is a single or double bond, so obtaining a compound of formula (I) wherein n and X are as defined above, === is a single or double bond, Y is an oxo group, and $R_1$ and $R_2$ are the same halogen; or (D) reacting a compound of formula (IV)

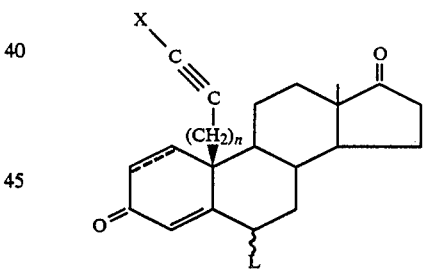

(IV)

wherein
n and X are as defined above, === is a single or double bond and L is a leaving group displaceable by nucleophilic substitution, with a compound of formula (V)

M—N₃    (V)

wherein
M is an alkali metal or ammonium cation or a tri-$C_1$–$C_6$-alkyl silyl group, so obtaining a compound of formula (I) wherein n and X are as defined above, === is a single or double bond, Y is an oxo group, $R_2$ is hydrogen and $R_1$ is an azido group, and, if desired, converting a compound of formula (I) into another compound of formula (I) and/or, if desired, salifying a compound of formula (I) containing a salifiable group or obtaining a free compound of formula (I) from a salt thereof and/or, if desired, separating a mixture of isomers of formula (I) into the single isomers. The Vilsmeier reagent used for reaction with the compound (II) may be, e.g., of the kind described by K. Annen, in synthesis, 34 (1982) such as, for instance, formaldehyde dimethyl acetal or formaldehyde diethyl acetal and phosphoryl chloride.

The reaction between the compound (II) and the Vilsmeier reagent, to give a compound of formula (I) wherein Y is an oxo group, $\equiv\equiv\equiv$ is single bond, $R_2$ is hydrogen and $R_1$ is $C_1$–$C_6$ alkylidene, may be performed according to known methods, e.g. according to the method of K. Annen, in the hereabove cited reference.

Preferably a compound of formula (II) is reacted with unsubstituted or appropriately $C_1$–$C_6$ alkyl-substituted formaldehyde-diethylacetal in refluxing chloroform, in the presence of catalytic amounts of phosphoryl chloride and sodium acetate.

Alternatively the same reaction may be carried out in other inert solvents, e.g. 1,2-dichloroethane, diethylether or dioxane, and in the presence of other suitable condensing agents, e.g. phosphorus pentoxide or p-toluenesulfonic acid.

The halogenation of a compound of formula (IIa) to obtain a corresponding compound of formula (I) wherein $R_1$ is halogen may be carried out according to known methods, e.g. by treatment with a N-halosuccinimide or acetamide, e.g. N-bromosuccinimide or N-bromoacetamide, in a halogenated organic solvent such as, e.g., carbon tetrachloride, in accordance with the procedure described by C. Djerassi et al. in J. Am. Chem. Soc., 72, 4534 (1950).

The halogenation of a compound of formula (III), in order to obtain a corresponding compound of formula (I) wherein $R_1$ and $R_2$ are the same halogen may be carried out according to known methods, e.g. by treatment with molecular halogen, e.g. chlorine or bromine, in a suitable acidic solvent, preferably acetic acid, at a temperature ranging, e.g., from about 5° C. to about the room temperature.

In a compound of formula (IV) the leaving group L may be a halogen atom or a group $-O-SO_2-R_5$ or $-O-CO-R_6$ wherein $R_5$ is the residue of a sulfonic acid, e.g. methanesulfonic, trifluoromethanesulfonic or p-toluenesulfonic, and $R_6$ is the residue of a carboxylic acid either aliphatic, such as, e.g. acetic, or aromatic, such as, e.g. benzoic.

When L is halogen, preferred halogens are chlorine, bromine and iodine; when L is a group $-O-SO_2-R_5$, preferred groups are methanesulfonyloxy, trifluoromethanesulfonyloxy and p-toluenesulfonyloxy; when L is a group $-O-CO-R_6$, preferred groups are acetoxy and benzoyloxy.

When M in a compound of formula (V) is an alkali metal, this is preferably sodium or lithium; when M is a tri-$C_1$-$C_6$-alkylsilyl group, trimethylsilyl and dimethyl-tert-butylsilyl are preferred. Accordingly, preferred compounds of formula (V) are sodium azide, lithium azide, trimethylsilylazide or dimethyltert-butylsilyl azide.

The reaction between a compound of formula (IV) and a compound of formula (V) is preferably carried out in an organic solvent such as, for instance, N,N-dimethylformamide, N,N-dimethylacetamide or dimethylsulfoxide; some water or an aqueous alcoholic, e.g. methanolic or ethanolic, solution may be added, if desired, to increase the solubility of the azide of formula (V).

The reaction is preferably performed at a temperature from, e.g., about 0° C. to about the room temperature and reaction times are preferably short, e.g., from some minutes to about one hour.

Optional conversions of a compound of formula (I) into another compound of formula (I) include, for example, (i) the halogenation of a compound of formula (I) wherein X is hydrogen and $R_1$ is a group $C_1$-$C_6$ alkylidene, to obtain a corresponding compound of formula (I) wherein X is halogen; (ii) the dehydrogenation of a compound of formula (I) wherein $\equiv\equiv\equiv$ is a single bond and $R_1$ is halogen or $C_1$-$C_6$ alkylidene, $R_2$ being hydrogen, to obtain a corresponding compound of formula (I) wherein $\equiv\equiv\equiv$ is a double bond; (iii) the reduction of a compound of formula (I) wherein $R_1$ is azido to obtain a corresponding compound of formula (I) wherein $R_1$ is a group

where $R_3$ and $R_4$ are both hydrogen; (iv) the alkylation of a compound of formula (I) wherein $R_1$ is a group

wherein $R_3$ and $R_4$ are both hydrogen to obtain a corresponding compound of formula (I) wherein $R_1$ is a group

wherein at least one of $R_3$ and $R_4$ is $C_1$-$C_4$ alkyl; and (v) the conversion of a compound of formula (I) wherein Y is an oxo group into a corresponding compound of formula (I) wherein Y is a group methylene.

The optional halogenation of a compound of formula (I) wherein X is hydrogen and $R_1$ is $C_1$-$C_6$ alkylidene to obtain a corresponding compound of formula (I) wherein X is halogen, may be carried out following conventional halogenation procedures. For example a compound of formula (I) wherein X is bromine or iodine, may be obtained by reaction with, e.g., an equimolar amount of N-bromo- or N-iodo-succinimide in the presence of catalytic amounts of silver nitrate.

The halogenation reaction is generally performed in acetone, but other solvents such as, e.g., tetrahydrofuran, ethanol or 1-methyl-2-pyrrolidone can be used: R. Wiechert et al. Angew. Chem. Int. Ed. 23 (1984)9, 727–728.

A compound of formula (I) wherein X is chlorine or fluorine may be obtained, for instance, by first treatment with a strong base, e.g. sodium hydride, potassium hydride, methyllithium, butyllithium, potassium tert-butoxide, or with a Grignard reagent, e.g. methylmagnesium bromide, ethylmagnesium bromide, and then with a source of positive chlorine or fluorine, e.g. respectively, with N-chloro succinimide or a N-fluoro-N-alkylsulfonamide or perchloryl fluoride, according to, e.g., the methods described by W. Verboom et al., [Synthesis 296–297 (1979)] and by W. E. Barnette [J.A.C.S. 106, 452–454 (1984)].

The optional dehydrogenation of a compound of formula (I) where --- is a single bond and $R_1$ is halogen or $C_1$–$C_6$ alkylidene to obtain a corresponding compound of formula (I) wherein --- is a double bond, may be, e.g., performed by treatment with 2,3-dichloro-5,6-dicyanobenzoquinone (DDQ) operating, for instance, in an inert solvent such as, e.g., dioxane, benzene, toluene, dichloromethane at a temperature ranging from about 40° C. to about 100° C. for reaction times ranging from about 12 hours to about 75 hours.

The optional reduction of a compound of formula (I) wherein $R_1$ is azido to obtain a corresponding compound of formula (I) wherein $R_1$ is a group

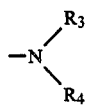

wherein $R_3$ and $R_4$ are both hydrogen may be performed by known methods using various reducing agents.

For example, the reduction may be carried out using propane-1,3-dithiol/triethylamine according to the method of Hagan Bayley et al [Tetr. Lett. 39, 3633 (1978)], or using dithiothreitol in aqueous solution, or mercaptoacetic acid/triethylamine, and others, or also by catalytic way with, e.g., the $H_2$/Pd/$H_2$-Lindlar catalyst, operating in an organic solvent, for instance in alcoholic, e.g. methanolic or ethanolic, medium, at a temperature from, e.g., the room temperature to about 100° C., for reaction times which may vary from few minutes to several hours.

The optional alkylation of a compound of formula (I) wherein $R_1$ is a group

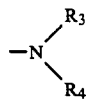

wherein $R_3$ and $R_4$ are both hydrogen to obtain a corresponding compound of formula (I) wherein $R_1$ is a group

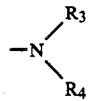

wherein at least one of $R_3$ and $R_4$ is $C_1$–$C_4$ alkyl, may be carried out by reaction with a suitable alkylating agent which may be e.g. a $C_1$–$C_4$ alkyl halide, in particular iodide, or di-alkyl-sulfate; for obtaining a compound of formula (I) wherein $R_1$ is a group

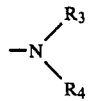

wherein at least one of $R_3$ and $R_4$ is methyl or ethyl suitable alkylating agents are, e.g., methyl iodide, dimethylsulfate or, respectively, ethyliodide and diethylsulfate.

Reaction conditions well known to the skilled in the art and well described in the organic chemistry may be followed: see, e.g., Lucier et al, Org. Synth. 44, 72 (1964).

The optional conversion of a compound of formula (I) wherein Y is an oxo group, into the corresponding compound of formula (I) wherein Y is a group methylene, may be, e.g., carried out by treatment with a Wittig reagent of formula $(\phi)_3P^+$—$CH_3.Hal^{(-)}$ wherein $\phi$ is a phenyl or $C_1$–$C_6$ alkyl group and Hal is bromine or iodine, following conventional procedures.

For example the reaction may be carried out using an equimolar amount of the Wittig reagent, operating in an inert organic solvent, such as, for instance, diethylether, tetrahydrofuran, n-hexane, dimethylsulfoxide, dimethylformamide or hexamethylphosphoramide, and in the presence of a base which may be, for example, sodium hydride or potassium tert-butoxide, at a temperature between about 0° C. and the reflux temperature of the used solvent, preferably at room temperature.

Using in the above reaction an equimolar amount of the Wittig reagent, the 3-oxo group is made to react selectively with respect to the 17-oxo group; alternatively the latter group may be selectively protected in a conventional manner, before the Wittig reaction.

The optional salification of a compound of formula (I) containing a salifiable group and the preparation of a free compound from a salt may be performed in a conventional way, and conventional methods, e.g. fractional crystallization or chromatography, may be followed also for the optional separation of a mixture of isomers of formula (I) into the single isomers.

The compounds of formula (II) wherein X is hydrogen or $C_1$–$C_4$ alkyl either are known compounds, as described, e.g., in U.S. Pat. No. 4,322,416, or can be prepared from known compounds by known methods, e.g. those described in the hereabove said U.S. patent.

The compounds of formula (II) wherein X is halogen may be, e.g., prepared halogenating a corresponding compound of formula (II) wherein X is hydrogen following, for instance, the halogenation procedure described before in this specification for the transformation of a compound of formula (I) wherein X is hydrogen into a corresponding one wherein X is halogen.

In an alternative route, a compound of formula (II) wherein X is halogen may be prepared oxidizing a compound of formula (VI)

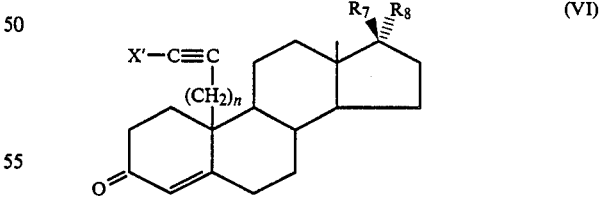

wherein
n is as defined above; X' is halogen; one of $R_7$ and $R_8$ is hydrogen and the other is hydroxy, through the use of known oxidizing agents, e.g. with dicyclohexylcarbodiimide, pyridine and trifluoroacetic acid (the Moffatt's reagent) or with the Jones' or the Sarett's reagent.

The compounds of formula (IIa) wherein --- is single bond are compounds of formula (II) and so can be prepared as hereinbefore indicated.

The compounds of formula (IIa) wherein --- is double bond may be, e.g., prepared from the corresponding ones wherein === is single bond by treatment with a suitable dehydrogenating agent, for instance with 2,3-dichloro-5,6-dicyano-benzoquinone (DDQ) in analogous way as described above for the same dehydrogenation step on the compounds of formula (I). Optionally, a compound of formula (IIa) wherein === is double bond and X is halogen, can also be obtained halogenating a corresponding compound of formula (IIa) wherein X is hydrogen operating in analogous fashion as indicated before for the same transformation on a compound of formula (I) or (II).

The compounds of formula (III) are either known compounds, as described e.g. in U.S. Pat. No. 4,322,416, or compounds that can be prepared by known methods from known compounds. They can be, e.g., obtained by dehydrogenation reactions on compounds (II). For example, the compound of formula (II) may be first dehydrogenated with, e.g., chloranil (i.e. 2,3,5,6-tetrachloro-1,4-benzoquinone) to give the corresponding compound of formula (III) wherein === is single bond, i.e. the 4,6-diene derivative, which, if desired, may be further dehydrogenated with, e.g., 2,6-dichloro-5,6-dicyano-benzoquinone (DDQ), to give the corresponding compound of formula (III) wherein === is double bond, i.e. the 1,4,6-triene derivative. The latter may also be obtained, alternatively, dehydrogenating first the compound (II) with, e.g., DDQ, to the corresponding 1,4-diene derivative and then dehydrogenating this with, e.g., chloranil.

Dehydrogenation with DDQ may be performed, e.g., by the same procedure previously described in this specification for analogous dehydrogenations with the same reagent. Dehydrogenation with chloranil may be, e.g., carried out operating in an inert solvent such as, e.g., methanol, ethanol, tert.butanol or higher aliphatic alcohols at a temperature ranging, e.g. from about 40° C. to about 120° C. and for reaction times ranging from about 12 hours to about 72 hours.

The compounds of formula (IV) wherein L is halogen are compounds of the invention and thus can be obtained as previously described in this specification.

The compounds of formula (IV) wherein L is a group $-OSO_2-R_5$ or $-O-CO-R_6$ as defined above may be obtained esterifying the corresponding 6-hydroxy derivatives with the appropriate sulfonic or carboxylic acid or, preferably, with a reactive derivative thereof, e.g. sulfonyl or acyl halide, in particular the chloride, or the anhydride, following conventional esterification procedures.

The said 6-hydroxy-derivatives may be, in their turn, prepared from known compounds by known methods. The compounds of formula (V) are known compounds. The compounds of formula (VI) may be prepared by the reaction steps herebelow schematized:

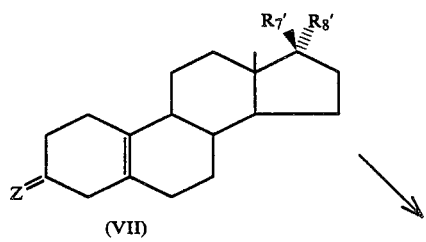

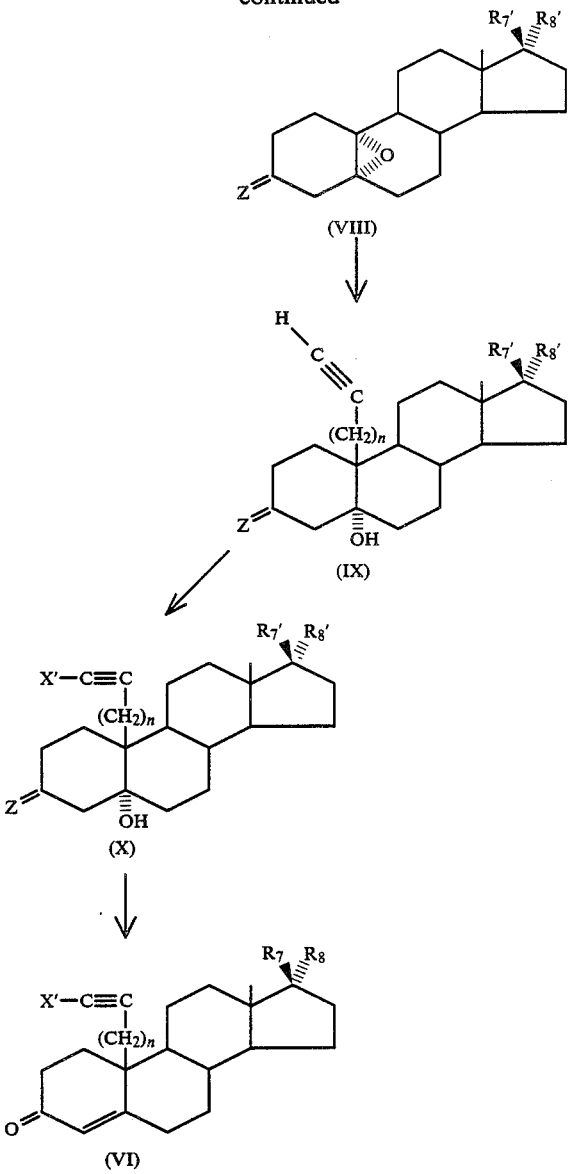

wherein n and X′ are as defined above, Z is a protected oxo group, preferably an ethylenedioxy group, one of R′$_7$ and R′$_8$ is hydrogen and the other is a free or protected hydroxy.

When one of R′$_7$ and R′$_8$ is a protected hydroxy, it is, e.g., a hydroxy group esterified with a carboxylic acid, either a $C_2$–$C_7$ aliphatic carboxylic acid such as, e.g., acetic acid, or an aromatic carboxylic acid such as, e.g., benzoic acid.

The compounds of formula (VII) are known in the chemistry literature (see, e.g., H. J. Ringold, J. Am. Chem. Soc. 78, 2477, 1956) or can be prepared from known compounds following known methods as those reported, for instance, in: Fieser et al, "Steroids", Reinhold, New York, 1959; Djerassi, Ed., "Steroid Reactions", Holden Day, San Francisco, 1963; and J. Fried, J. A. Edwards "Organic Reactions in Steroid Chemistry", Van Nostrand Reinhold Company, N.Y., 1972). According to the above reaction sequence a compound of formula (VII) is first epoxidized to give a compound of formula (VIII).

The epoxidation may be performed according to known methods, for example by treatment with a N-halo-succinimide or N-halo-acetamide (e.g., N-bromosuccinimide or N-chloroacetamide) in a solvent such as, e.g., dimethylformamide or dimethylsulfoxide, to obtain the corresponding halohydrine, and sequential dehydrohalogenation in alkaline medium (e.g. with a sodium alkoxide, e.g. methoxide) to obtain a sterically pure 5α,10α-epoxide (Lucien Nedelec, Bull. Soc. Chim. France 7, 2548, 1970).

A compound of formula (VIII) so obtained is reacted with a metallorganic compound carrying a H—C≡C—(CH$_2$)$_n$— moiety, wherein n is as defined above, to give a compound of formula (IX). The organometallic compound may be, for example, a Grignard compound H—C≡C—(CH$_2$)$_n$MgHal wherein Hal is a halogen atom, preferably chlorine, bromine or iodine, prepared according to known methods: L. Brandsma and H. D. Werkruijsse, Synth. Acetylenes, Allenes and Cumulenes, 1981, 16. The reaction may be, e.g., carried out in a solvent chosen from tetrahydrofurane, tetrahydropyrane, γ-dihydropyrane, diethylether, anisole, and furane, e.g. at a temperature from about −30° C. to the room temperature, preferably between −5° C. and +10° C.

For the conversion (halogenation) of a compound of formula (IX) into a compound of formula (X), wherein X' is halogen, conventional halogenation procedures may be followed, for example the compound of formula (IX) may be transformed into a compound of formula (X) wherein X' is bromine or iodine, by reaction with, e.g., an equimolar amount of N-bromo- or N-iodo-succinimide in the presence of catalytic amounts of silver nitrate.

The halogenation reaction is generally performed in acetone, but other solvents such as, e.g., tetrahydrofurane, ethanol or 1-methyl-2-pyrrolidone can be used: R. Wiechert et al, Angew. Chem. Int. Ed. 23 (1984)9, 727–728.

A compound of formula (IX) may be transformed into a compound of formula (X) wherein X' is chlorine or fluorine, for instance by treating it first with a strong base, e.g. sodium hydride, potassium hydride, methyllithium, butyllithium, potassium tert-butoxide, or with a Grignard reagent, e.g. methylmagnesium bromide, ethylmagnesium bromide, and then with a source of positive chlorine or fluorine, e.g., respectively, with N-chloro succinimide or a N-fluoro-N-alkylsulfonamide or perchloryl fluoride, according to, e.g., the methods described by W. Verboom et al., [Synthesis 296–297 (1979)] and by W. E. Barnette [J.A.C.S. 106, 452–454 (1984)].

The compound of formula (X) is then dehydrated and deprotected to give a compound of formula (VI). This step may be carried out with a suitable dehydrating agent which may be, for example, a mineral, preferably concentrated, acid such as, for instance, hydrochloric or sulfuric acid, or with a sulfonic resin as well.

The reaction may be performed in an inert, organic, preferably anhydrous, solvent, such as, for instance, methanol, ethanol, benzene, toluene, n-hexane or cyclohexane, at a temperature varying approximately between about 0° C. and about 50° C., preferably at room temperature.

Oxo protecting groups are removed during the dehydration process; hydroxy protecting groups possibly present, e.g. ester groups as defined above, may be removed by conventional saponification procedures.

The compounds of the present invention are inhibitors of the biotransformation of androgens into estrogens, i.e. they are, as already said, steroidal aromatase inhibitors.

By virtue of their ability to decrease estrogen levels, these compounds can be useful in the treatment of various estrogen dependent diseases, i.e., breast, endometrial, ovarian and pancreatic cancers, gynecomastia, benign breast disease, endometriosis and polycystic ovarian disease.

Another application of the compounds of the invention is in the therapeutic and/or prophylactic treatment of prostatic hyperplasia, a disease of the estrogen dependent stromal tissue.

The aromatase inhibitors of formula (I) can find also use in the treatment of male infertility associated with oligospermia and for female fertility control, by virtue of their ability to inhibit ovulation and egg nidation.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion; intravaginally; or topically. The dosage depends on the age, weight, conditions of the patient and administration route; for example the dosage adopted for oral administration to adult humans may range from about 10 to about 200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidine; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carrier only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solution for intravenous injections or infusions may contain as carrier, for example, sterile water or preferably they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

The vaginal tablets may contain, together with the active compound, a pharmaceutically acceptable carrier, e.g. cocoa-butter, polyethylene glycol, a polyoxyethylene sorbitan fatty acid ester surfactant of lecithin. Compositions for topical application such as, e.g., creams, lotions or pastes, may be, e.g., prepared by admixing the active ingredient, with a conventional oleaginous or emulsifying excipient.

The following examples illustrate but do not limit the invention.

EXAMPLE 1

10β-(2-propynyl)-6-methylenestr-4-ene-3,17-dione [I, X=H, R$_2$=H, R$_1$=CH$_2$, Y=O, n=1, === =single bond]

A mixture of sodium acetate (1.79 g), absolute chloroform (53 ml), formaldehyde diethyl acetal (54 ml), phosphoryl chloride (6.80 ml) and 10β-(2-propynyl)estr-4-ene-3,17-dione (3.0 g) is stirred for 2 hours at room temperature.

To the stirred reaction mixture, cooled to room temperature, are added in the order 70 ml of saturated aqueous solution of potassium carbonate, 36 ml of 2N aqueous sodium hydroxide and 70 ml of water; the mixture is then stirred for an additional hour.

The layers are separated and the aqueous phase is extracted with ethyl acetate (5×50 ml); the combined organic extracts are washed with water (3×20 ml) and dried over Na$_2$SO$_4$. Evaporation of the solvent and crystallization of the crude from diethylether:n-hexane (2:1 40 ml) gives 1,5 g of solid material that is further purified by flash chromatography on SiO$_2$ eluting with n-hexane:ethyl acetate 40:60, so obtaining 1.26 g of the title compound as a white crystalline product, m.p. 190°–191° C., N.M.R. (CDCl$_3$)δ: 0.95 (3H, s); 2.03 (1H, t); 5.00 (1H, bs); 5.15 (1H, bs); 6.02 (1H, bs).

IR (nujol)cm$^{-1}$: 3230, 2110, 1730, 1675, 1630, 1610, 915.

By proceeding analogously the following compounds can be prepared:

10β-(3-iodo-2-propynyl)-6-methylenestr-4-ene-3,17-dione;
10β-(3bromo-2-propynyl)-6-methylenestr-4-ene-3,17-dione;
10β-(3-chloro-2-propynyl)-6-methylenestr-4-ene-3,17-dione;
10β-(3-fluoro-2-propynyl)-6-methylenestr-4-ene-3,17-dione.

EXAMPLE 2

10β-(2-propynyl)-6β-bromoestr-4-ene-3,17-dione [I, X=H, R$_2$=H, R$_1$=Br, Y=O, n=1, === =single bond; IV, X=H, L=Br, n=1, (a)=single bond]

To a solution of 165 mg of 10β-(2-propynyl)estr-4-ene-3,17-dione in 4 ml of carbon tetrachloride, 104 mg of N-bromo-succinimide and some little crystals of benzoylperoxide are added. The mixture is refluxed for 2 hours and then filtered while still hot, to eliminate the formed succinimide.

The filtrate is diluted with 50 ml of methylenechloride, washed with water, diluted sodium sulphite solution, and water, and then dried over anhydrous sodium sulphate. The solvent is evaporated under reduced pressure and the crude is chromatographed on SiO$_2$ eluting with n-hexane:ethyl acetate 6:4 to give 100 mg of the title compound as a yellowish foam, IR (nujol)cm$^{-1}$: 3222, 2125, 1740, 1670, 1620.

N.M.R. (CDCl$_3$) δ: 0.95 (3H, s); 2.03 (1H, t); 4.85 (1H, m); 5.80 (1H, bs).

By proceeding analogously the following compounds can be prepared:

10β-(3-iodo-2-propynyl)-6β-bromoestr-4-ene-3,17-dione;
10β-(3-bromo-2-propynyl)-6β-bromoestr-4-ene-3,17-dione;
10β-(3-chloro-2-propynyl)-6β-bromoestr-4-ene-3,17-dione;
10β-(3-fluoro-2-propynyl)-6β-bromoestr-4-ene-3,17-dione;
10β-(2-propynyl)-6β-bromoestra-1,4-diene-3,17-dione;
10β-(3-iodo-2propynyl)-6β-bromoestra-1,4-diene-3,17-dione;
10β-(3-bromo-2-propynyl)-6β-bromoestra-1,4-diene-3,17-dione;
10β-(3-chloro-2-propynyl)-6β-bromoestra-1,4-diene-3,17-dione;
10β-(3-fluoro-2-propynyl)-6β-bromoestra-1,4-diene-3,17-dione.

EXAMPLE 3

10β-(2-propynyl)-6-methylenestra-1,4-diene-3,17-dione [I, X=H, R$_2$=H, R$_1$=CH$_2$, Y=O, n=1, === =double bond]

To a solution of 480 mg of 10β-(2-propynyl)-6-methylenestr-4-ene-3,17-dione in 15 ml of dioxane are added 511 mg of dichlorodicyanoquinone (DDQ) and 571 mg of p-toluenesulfonic acid, and the mixture is refluxed for half an hour.

The dioxane is evaporated under vacuum and the dark residue is dissolved in 100 ml of ethyl acetate:water 1:1; the organic phase is separated and the aqueous layer is extracted twice with ethyl acetate; the combined organic extracts are washed with water (3×10 ml) and dried over anhydrous sodium sulphate.

The solvent is evaporated and the residue is purified by flash chromatography on silica gel eluting with ethyl acetate:n-hexane 50:50 to give the title compound, m.p. 175°–176° C. (from ethyl acetate/n-hexane);

N.M.R. (CDCl$_3$) δ: 0.93 (3H, s); 1.90 (1H, t); 2.59 (2H, d); 5.02 (1H, t); 5.13 (1H, t); 6.27 (1H, d); 6.41 (1H, dd); 7.00 (1H, d).

IR (nujol)cm$^{-1}$: 3220, 2110, 1730, 1670, 1636, 1620, 1602, 915.

By proceeding analogously the following compounds can be prepared:

10β-(3-iodo-2-propynyl)-6-methylenestra-1,4-diene-3,17-dione;
10β-(3-bromo-2propynyl)-6-methylenestra-1,4-diene-3,17-dione;
10β-(3-chloro-2-propynyl)-6-methylenestra-1,4-diene-3,17-dione;

10β-(3-fluoro-2-propynyl)-6-methylenestra-1,4-diene-3,17-dione;
10β-(2-propynyl)-6β-bromoestra-1,4-diene-3,17-dione;
10β-(3-iodo-2-propynyl)-6β-bromoestra-1,4-diene-3,17-dione;
10β-(3-bromo-2-propynyl)-6β-bromoestra-1,4-diene-3,17-dione;
10β-(3-chloro-2-propynyl)-6β-bromoestra-1,4-diene-3,17-dione;
10β-(3-fluoro-2-propynyl)-6β-bromoestra-1,4-diene-3,17-dione.

EXAMPLE 4

10β-(2-propynyl)-6α-azidoestr-4-ene-3,17-dione [I, X=H, R$_2$=H, R$_1$=N$_3$, Y=O, n=1, --- =single bond]

A mixture of 234.6 mg of 10β-(2-propynyl)-6β-bromoestr-4-ene-3,17-dione, 11.5 ml of dimethylformamide, 0.4 ml of distilled water and 50 mg of NaN$_3$ are stirred at room temperature for some minutes to obtain an homogeneous solution; this is then left in the dark overnight.

The mixture is poured into water and extracted with ethyl acetate (3×50 ml) and the organic layers are separated and dried over anhydrous sodium sulphate.

Removal of the solvent under vacuo makes a white crystalline product precipitate; this is collected by filtration and dried to give 150 mg of crystalline title compound, m.p. 205°-206° C., N.M.R. (CDCl$_3$) δ: 0.98 (3H, s); 2.03 (1H, t); 4.31 (H$_{6β}$, ddd, J$_I$~12 Hz az/ax, J$_{II}$~5 Hz, ax/eq, J$_{III}$~2 Hz H$_4$/H$_6$); 5.80 (1H, bs).

IR (nujol)cm$^{-1}$: 3222, 2125, 2090, 1740, 1670, 1600.

By proceeding analogously, the following compounds can be prepared:
10β-(3-iodo-2-propynyl)-6α-azidoestr-4-ene-3,17-dione;
10β-(3-bromo-2-propynyl)-6α-azidoestr-4-ene-3,17-dione;
10β-(3-chloro-2-propynyl)-6α-azidoestr-4-ene-3,17-dione;
10β-(3-fluoro-2-propynyl)-6α-azidoestr-4-ene-3,17-dione;
10β-(2-propynyl)-6α-azidoestra-1,4-diene-3,17-dione;
10β-(3-iodo-2-propynyl)-6α-azidoestra-1,4-diene-3,17-dione;
10β-(3-bromo-2-propynyl)-6α-azidoestra-1,4-diene-3,17-dione;
10β-(3-chloro-2-propynyl)-6α-azidoestra-1,4-diene-3,17-dione;
10β-(3-fluoro-2-propynyl)-6α-azidoestra-1,4-diene-3,17-dione.

EXAMPLE 5

10β-(2-propynyl)-6α-aminoestr-4-ene-3,17-dione [I, X=H, R$_2$=H, R$_1$=NH$_2$, Y=O, n=1, --- =single bond]

In a three necked flask purged with dry nitrogen, 816 mg of 10β-(2-propynyl)-6-azidoandrost-4-ene-3,17-dione are dissolved in 120 ml of dry, freshly distilled methanol. To the yellow slurry stirred under nitrogen atmosphere are added 1.8 ml of propane-1, 3-dithiol and 2,4 ml of triethylamine. After 0.5 hours stirring at room temperature the solution is completed; the stirring is continued at room temperature for 7 hours to complete the reaction. The reaction mixture is poured into water, acidified to pH 2 with 1N aqueous hydrochloric acid and extracted with diethylether. The organic phase is discharged and the aqueous phase is basified with 2N aqueous sodium hydroxide solution. The crystalline precipitate is collected by filtration and dried to yield 590 mg of crude which is crystallized from ethyl acetate/n-hexane to give 500 mg of the title compound, N.M.R. (CDCl$_3$)δ: 0.95 (3H, s); 1.95 (1H, t), 2.90 (2H, m, NH$_2$), 5.80 (1H, bs).

IR (nujol) cm$^{-1}$: 3430, 3350, 3222, 2125, 1740, 1670, 1620.

By proceeding analogously the following compounds can be prepared:
10β-(3-iodo-2-propynyl)-6α-aminoestr-4-ene-3,17-dione;
10β-(3-bromo-2-propynyl)-6α-aminoestr-4-ene-3,17-dione;
10β-(3-chloro-2-propynyl)-6α-aminoestr-4-ene-3,17-dione;
10β-(3-fluoro-2-propynyl)-6α-aminoestr-4-ene-3,17-dione;
10β-(2-propynyl)-6α-aminoestra-1,4-diene-3,17-dione;
10β-(3-iodo-2-propynyl)-6α-aminoestra-1,4-diene-3,17-dione;
10β-(3-bromo-2-propynyl)-6α-aminoestra-1,4-diene-3,17-dione;
10β-(3-chloro-2-propynyl)-6α-aminoestra-1,4-diene-3,17-dione;
10β-(3-fluoro-2-propynyl)-6α-aminoestra-1,4-diene-3,17-dione.

EXAMPLE 6

10β-(2-propynyl)-6β,7α-dibromoestra-1,4-diene-3,17-dione [I, X=H, R$_1$=R$_2$=Br, Y=O, n=1, --- =double bond]

To a suspension of 551 mg of 10β-(2-propynyl)-estra-1,4,6-triene-3,17-dione in 20 ml of anhydrous diethylether, cooled with an ice-water bath, a solution of 0.1 ml of bromine in 6 ml of glacial acetic acid is added dropwise, under stirring, maintaining the internal temperature under +5° C. After 3 hours at room temperature, the acetic acid is removed under reduced pressure and the red residue is chromatographed on SiO$_2$ eluting with n-hexane: ethyl acetate:methylene chloride 50:10:40, thus obtaining 503 mg of the title compound, N.M.R. (CDCl$_3$)δ: 0.92 (3H, s), 1.95 (1H, t); 4.55 (1H, m); 5.05 (1H, d), 6.20 (s, 1H).

IR(nujol) cm$^{-1}$: 3220, 2125, 1740, 1670-60, 1630, 1605;

MS m/e: 466 (M$^+$·), 387 (M$^+$·-Br), 307 (387-HBr).

By proceeding analogously the following compounds can be prepared:
10β-(3-iodo-2-propynyl)-6β,7α-dibromoestra-1,4-diene-3,17-dione;
10β-(3-bromo-2-propynyl)-6β,7α-dibromoestra-1,4-diene-3,17-dione;
10β-(3-chloro-2-propynyl)-6β,7α-dibromoestra-1,4-diene-3,17-dione;
10β-(3-fluoro-2-propynyl)-6β,7α-dibromoestra-1,4-diene-3,17-dione;
10β-(2-propynyl)-6β,7α-dibromoestr-4-ene-3,17-dione;
10β-(3-iodo-2-propynyl)-6β,7α-dibromoestr-4-ene-3,17-dione;
10β-(3-bromo-2-propynyl)-6β,7α-dibromoestr-4-ene-3,17-dione;
10β-(3-chloro-2-propynyl)-6β,7α-dibromoestr-4-ene-3,17-dione;
10β-(3-fluoro-2-propynyl)-6β,7α-dibromoestr-4-ene-3,17-dione.

EXAMPLE 7

10β-(3-bromo-2-propynyl)-6-methylenestr-4-ene-3,17-dione [I, X=Br, R$_1$=CH$_2$, R$_2$=H, Y=O, n=1, ≡≡≡=single bond]

A solution of 484 mg of 10β-(2-propynyl)-6-methylenestr-4-ene-3,17-dione in 20 ml of acetone is treated at room temperature with 312 mg of N-bromosuccinimide and 25 mg of silver nitrate, and stirred 4 hours at room temperature in the dark. The mixture is poured with stirring into ice-water and the formed precipitate is filtered off and dissolved in ethyl acetate. The resulting solution is washed with water, dried, evaporated to dryness in vacuo, and the crude is purified by flash chromatography on SiO$_2$, eluting with n-hexane:diethylether 20:80 to give 363 mg of the title compound as a white crystalline product, m.p. 198°-200° C., dec.

N.M.R. (CDCl$_3$) δ: 0.95 (3H, s); 2.88 (2H, ABq); 5.01 (1H, bs); 5.16 (1H, bs); 6.05 (1H, bs).

IR (nujol) cm$^{-1}$: 1730, 1675, 1630, 1610, 915.

MS m/e: 401 (M$^+$·).

By proceeding analogously the following compounds can be prepared:

10β-(3-iodo-2-propynyl)-6-methylenestr-4-ene-3,17-dione;

10β-(3-iodo-2-propynyl)-6-methylenestra-1,4-diene-3,17-dione;

10β-(3-bromo-2-propynyl)-6-methylenestra-1,4-diene-3,17-dione.

EXAMPLE 8

5,10α-epoxy-17β-hydroxy-3,3-ethylendioxyestrane [VIII, Z=—O—CH$_2$—CH$_2$—O—, R'$_7$=OH, R'$_8$=H]

To a suspension of 8.5 g of 17β-acetoxy-3,3-ethylenedioxy-estr-5(10)-ene in 130 ml of dimethylformamide and 40 ml of water, 2.35 g of powdered CaCO$_3$ and 8.39 g of N-bromosuccinimide are added at room temperature. After stirring for 4 hours at room temperature, the yellow suspension is poured into ice-water and the precipitate filtered on buckner; the precipitate is dissolved in methylene chloride and the insoluble residue is filtered off; the filtrate is washed with water and dried over anhydrous sodium sulphate. Evaporation of the solvent yields 10.7 g of 17β-acetoxy-3,3-ethylenedioxy-5α-hydroxy-10β-bromo-estrane as a white solid material, m.p. 140° C., dec.

I.R. (nujol): cm$^{-1}$ 3600-3100, 1735, 1375.

N.M.R. (DMSO-d$_6$) δ: 0.66 (3H, s); 3.55 (1H, m); 3.90 (2H, m); 4.41 (1H, d); 4.48 (1H, s).

Into a two necked flask, kept under a nitrogen atmosphere, 10.7 g of 5α-hydroxy-17β-acetoxy-10β-bromo-3,3-ethylenedioxyestrane are suspended in 108 ml of anhydrous methanol and treated with 4.173 g of sodium methoxide for 20 hours at room temperature.

The solution is then diluted with methylene chloride (1 l) and washed with water, brine, water and finally anhydrified over sodium sulphate.

Evaporation of the solvent leaves 9.5 g of white solid material, which is purified by flash chromatography on silica gel. Eluting with n-hexane:ethyl acetate:triethylamine (50:50:0.1) gives 6.57 g of the title compound.

m.p. 96°-98° C. (diethylether).

I.R. (nujol): cm$^{-1}$ 3500.

N.M.R. (CDCl$_3$)δ: 0.77 (3H, s); 3.68 (1H, m); 3.90 (4H, m).

EXAMPLE 9

5α,17β-dihydroxy-10β-(2-propynyl)-3,3-ethylenedioxyestrane [IX, Z=—O—CH$_2$—CH$_2$—O—, R'$_7$=OH, R'$_8$=H, n=1]

Into a solution of 1.5 g of 5,10α-epoxy-17β-hydroxy-3,3-ethylenedioxyestrane in 40 ml of dry diethylether, cooled to 0° C. with an external ice-cooling bath, 28 ml of a 1.6M solution of propargylmagnesium bromide (prepared according to the method reported in "Synthesis of Acetylenes, Allenes and Cumulenes", L. Brandsma and H. D. Verkruysse, page 16, Elsevier Scientific Publishing Company—Amsterdam, Oxford, N.Y. 1981) are added in one portion, operating under nitrogen atmosphere.

The mixture is stirred at 0° C. for 18 hours, then 10 ml of saturated ammonium chloride aqueous solution are added dropwise, while cooling at 0° C.; after 10 minutes of additional stirring at 0° C. the solution is warmed to room temperature, diluted with 50 ml of saturated aqueous ammonium chloride solution and extracted with ethyl acetate; the organic phase is washed with water and dried over anhydrous sodium sulphate. The solvent is evaporated under vacuum and the residue (1.98 g) is purified by flash chromatography on silica gel, eluting with ethyl acetate:n-hexane:triethylamine 40:60:0.1, thus obtaining 1.119 g of the title compound as a colourless oil which is crystallized from ethyl acetate/n-hexane to give 1.119 g of crystalline compound.

m.p. 120°-121° C.; [α]$_D$+10.6° (c=1, CHCl$_3$).

I.R. (nujol): cm$^{-1}$ 3550, 3510, 3425, 3310, 3290, 2110, 840;

N.M.R. (CDCl$_3$) δ: 0.76 (3H, s); 2.39 (2H, m); 3.74 (1H, m); 3.95 (4H, bs); 4.15 (1H, s).

EXAMPLE 10

5α,17β-dihydroxy-10β-(3-bromo-2-propynyl)-3,3-ethylenedioxyestrane [X, Z=—O—CH$_2$—CH$_2$—, X'=Br, R'$_7$=OH, R'$_8$=H, n=1]

A solution of 374 mg of 5α,17β-dihydroxy-10β-(2-propynyl)-3,3-ethylenedioxyestrane in 15 ml of acetone is treated at room temperature with 316 mg of N-bromo succinimide and 34 mg of silver nitrate. After 4 hours the reaction mixture is poured, under stirring, into 150 ml of ice-water and the precipitate that is formed is filtered off and dissolved in ethyl-acetate.

The resulting solution is washed with water, dried over anhydrous sodium sulphate and evaporated to dryness in vacuo. The solid residue is purified by flash chromatography on silica gel eluting with ethylacetate:n-hexane:triethylamine (40:60:0.1), thus obtaining 264 mg of the title compound.

m.p. 134°-136° C.; [α]$_D$+19.0 (c=1, CHCl$_3$).

I.R. (nujol) cm$^{-1}$: 3520, 3470, 3400, 3290, 860.

N.M.R. (CDCl$_3$)δ: 0.76 (3H, s); 2.39 (2H, m); 3.74 (1H, m); 3.95 (4H, bs); 4.15 (1H, s).

By proceeding analogously the compound 5α,17β-dihydroxy-10β-(3-iodo-2-propynyl)-3,3-ethylenedioxyestrane can be prepared.

EXAMPLE 11

5α,17β-dihydroxy-10β-(3-chloro-2-propynyl)-3,3-ethylenedioxyestrane [X, Z=—O—CH$_2$—CH$_2$—O—, X'=Cl, R'$_7$=OH, R'$_8$=H, n=1]

To a solution of 374.5 mg of 5α,17β-dihydroxy-10β-(2-propynyl)-3,3-ethylenedioxyestrane in 3.0 ml of anhydrous tetrahydrofuran, a solution of salt-free methyllithium (1.1 mmol) in diethyl ether (1.5 ml) is added under dry nitrogen atmosphere at −50° C. Subsequently, hexamethylphosphoric acid triamide (1 ml) is added, keeping the temperature below −50° C. Stirring is continued for 15 minutes at −50° C., whereupon N-chloro-succinimide (201 mg) is added in small portions.

During the addition the reaction temperature of the mixture is allowed to rise to −15° C. After stirring at room temperature for 1.5 hour, the dark reaction mixture is poured into ice-water and the formed precipitate is filtered off and dissolved in ethyl acetate.

The resulting solution is washed with water, dried over anhydrous sodium sulphate and evaporated to dryness.

The solid residue is purified by flash chromatography on silica gel eluting with ethyl acetate:n-hexane:triethylamine 40:60:0.1 to give 246 mg of the title compound.

N.M.R. (CDCl$_3$)δ: 0.79 (3H, s); 2.35 (2H, m); 3.63 (1H, t); 3.98 (4H, bs); 4.23 (1H, s).

EXAMPLE 12

5α,17β-dihydroxy-10β-(3-fluoro-2-propynyl)-3,3-ethylenedioxyestrane [X, Z=—O—CH$_2$—CH$_2$—O—, X'=F, R'$_7$=OH, R'$_8$=H, n=1]

A solution of 202 mg of 5α,17β-dihydroxy-10β-(2-propynyl)-3,3-ethylenedioxyestrane in 5 ml of anhydrous tetrahydrofurane is cooled to −78° C. and 1.08 ml of 1.5M n-butyllithium in n-hexane is added dropwise.

After the reaction has proceeded for 30 minutes at −78° C., the solution is diluted with 10 ml of anhydrous toluene and then added dropwise to a solution of N-fluoro-N-methyl-p-tolyl-sulfonamide (164 mg) in 5 ml of anhydrous toluene, kept at −78° C. with an external dry-ice/acetone cooling bath. The reaction mixture is then allowed to rise to room temperature, and saturated aqueous ammonium chloride solution is added; extraction with ethyl acetate affords, after evaporation of the solvent, 250 mg of dark oil, which is purified by flash chromatography on silica gel to give 105 mg of the title compound.

N.M.R. (CDCl$_3$)δ: 0.78 (3H, s); 2.3 (2H, m); 3.63 (1H, t); 3.98 (4H, bs); 4.20 (1H, s).

EXAMPLE 13

17β-hydroxy-10β-(3-bromo-2-propynyl)estr-4-ene-3-one [VI, X'=Br, R$_7$=OH, R$_8$=H, n=1]

To a stirred solution of 453 mg of 5α,17β-dihydroxy-10β-(3-bromo-2-propynyl)-3,3-ethylenedioxyestrane in 10 ml of methanol, 3.3 ml of 5N hydrochloric acid aqueous solution are added and the mixture is stirred for 20 hours at room temperature. Then the mixture is poured into 100 ml of ice-water and extracted with ethyl acetate, the organic extracts are washed with brine, water and anhydrified over sodium sulphate. Evaporation of the solvent under vacuo affords 0.43 g of yellow oil, which is purified by flash chromatography on silica gel to give 304 mg of the title compound.

I.R. (nujol) cm$^{-1}$: 1660, 1620.

N.M.R. (CDCl$_3$)δ: 0.92 (3H, s); 3.63 (1H, t); 5.90 (1H, bs).

By proceeding analogously the following compounds can be prepared:

17β-hydroxy-10β-(3-iodo-2-propynyl)estr-4-en-3-one;

17β-hydroxy-10β-(3-chloro-2-propynyl)estr-4-en-3-one;

17β-hydroxy-10β-(3-fluoro-2-propynyl)estr-4-en-3-one.

EXAMPLE 14

10β-(3-bromo-2-propynyl)estr-4-ene-3,17-dione [II, X=Br, n=1]

To a solution of 1.173 g of 17β-hydroxy-10β-(3-bromo-2-propynyl)estr-4-en-3-one in 30 ml of acetone, cooled to −25° C. with an external cooling bath (acetone and dry-ice), 1.6 ml of 2.5M Jones reagent are added, dropwise, with stirring. After an additional stirring of 10 minutes, the excess of oxidant is destroyed by addition of 0.5 ml of isopropyl alcohol. the solution if diluted with 200 ml of benzene and left to rise to room temperature. The organic layer is separated and washed with saturated ammonium sulphate aqueous solution, with water and then dried over anhydrous sodium sulphate. Evaporation of the solvent under vacuo affords 1.30 g of solid material, which is purified by flash-chromatography on silica gel, eluting with n-hexane:diethylether 20:80, to give 1.13 g of the title compound as a crystalline product.

m.p. 180°–182° C., dec.; [α]$_D$+216° (c=1, CHCl$_3$).

I.R. (nujol) cm$^{-1}$: 1730, 1680, 1630.

N.M.R. (CDCl$_3$) δ: 0.92 (3H, s); 5.90 (1H, bs).

By proceeding analogously the following compounds can be prepared:

10β-(3-iodo-2-propynyl)estr-4-ene-3,17-dione;

10β-(3-chloro-2-propynyl)estr-4-ene-3,17-dione;

10β-(3-fluoro-2-propynyl)estr-4-ene-3,17-dione.

EXAMPLE 15

10β-(3-bromo-2-propynyl)estra-1,4-diene-3,17-dione [IIa, X=Br, n=1, === =double bond]

A mixture of 188 mg of 10β-(3-bromo-2-propynyl)estr-4-ene-3,17-dione and 376 mg of dichlorodicyanoquinone in 12.5 ml of dioxane is refluxed for 20 hours. The mixture is cooled and diluted with diethyl ether, then washed with aqueous sodium carbonate solution and dried. The solvent is evaporated and the residue is purified by flash chromatography on silica gel eluting with ethyl acetate:n-hexane 30:70 to give the title compound.

m.p. 202°–204° C., dec.

U.V.: λ$_{max}^{EtOH}$ 241 nm (10,435).

N.M.R. (CDCl$_3$)δ: 0.94 (3H, s); 2.75 (2H, m); 6.17 (1H, bs); 6.38 (1H, d); 7.31 (1H, d).

By proceeding analogously, the following compounds can be prepared:

10β-(3-iodo-2-propynyl)estra-1,4-diene-3,17-dione, m.p. 180°–182° C., dec.

10β-(3-chloro-2-propynyl)estra-1,4-diene-3,17-dione;

10β-(3-fluoro-2-propynyl)estra-1,4-diene-3,17-dione.

EXAMPLE 16

10β-(3-bromo-2-propynyl)estra-4,6-diene-3,17-dione [III, X=Br, n=1, --- =single bond]

A mixture of 313 mg of 10β-(3-bromo-2-propynyl)estr-4-ene-3,17-dione and 575 mg of chloranil in 21 ml of tert-butyl alcohol is heated at reflux for 2 hours. The mixture is diluted with ethyl acetate and filtered and the filtrate is washed with aqueous 1N sodium hydroxide, with brine and dried over sodium sulphate. The solvent is then evaporated and the residue chromatographed on silica gel using ethylacetate/n-hexane to give 140 mg of the title compound.

U.V.: $\lambda_{max}^{EtOH}$ 287 nm (18,035).

N.M.R. (CDCl$_3$)δ: 0.92 (3H, s); 2.75 (2H, m); 2.99 (1H, m); 5.78 (1H, bs); 7.23 (2H, m).

By proceeding analogously the following compounds can be prepared:

10β-(3-iodo-2-propynyl)estra-4,6-diene-3,17-dione;
10β-(3-chloro-2-propynyl)estra-4,6-diene-3,17-dione;
10β-(3-fluoro-2-propynyl)estra-4,6-diene-3,17-dione.

EXAMPLE 17

10β-(3-bromo-2-propynyl)estra-4,6-triene-3,17-dione [III, X=Br, n=1, ═══ =double bond]

A mixture of 500 mg of 10β-(3-bromo-2-propynyl)estra-4,6-diene-3,17-dione and 1.60 g of 2,3-dichloro-5,6-dicyanobenzoquinone in 20 ml of dioxane is refluxed for 3 hours. The mixture is diluted with ethyl acetate and filtered, and the filtrate is washed with aqueous 1N sodium hydroxide, with brine and dried over sodium sulphate. The solvent is then evaporated and the residue chromatographed on silica-gel using ethyl acetate/n-hexane to give 100 mg of the title compound.

U.V.: $\lambda_{max}^{EtOH}$ 225 nm (10,580), 254 nm (10,000), 298 nm (10,230);

N.M.R. (CDCl$_3$)δ: 0.92 (3H, s); 6.12 (1H, dd); 6.50 (1H, dd); 6.35 (1H, d); 7.15 (1H, d).

By proceeding analogously the following compounds can be prepared:

10β-(3-iodo-2-propynyl)estra-1,4,6-triene-3,17-dione;
10β-(3-chloro-2-propynyl)estra-1,4,6-triene-3,17-dione;
10β-(3-fluoro-2-propynyl)estra-1,4,6-triene-3,17-dione.

EXAMPLE 18

10β-(2-propynyl)-3,6-dimethylenestr-4-en-17-one [I, X=H, R$_2$=H, R$_1$=CH$_2$, Y=CH$_2$, n=1, ═══ =single bond]

To a solution of 302 mg of 10β-(2-propynyl)-6-methylenestra-4-ene-3,17-dione in 2 ml of anhydrous dimethylsulfoxide, 3.75 ml of a 4N solution of methylene-triphenylphosphonium ylide (obtained by portionwise addition of 1.96 g of methyl-triphenyl-phosphonium iodide to a solution of 449 mg of potassium tert.butoxide in 10 ml of anhydrous dimethylsulfoxide, while cooling to about 18° C.) are added dropwise at room temperature in 5 hours. The mixture is poured into water and extracted with ethyl acetate, the organic extracts are washed with water, dried over Na$_2$SO$_4$ and the solvent rmoved under vacuum. The crude is chromatographed on silica gel eluting with n-hexane:diethylether 40:60 to give 130 mg of the title compound.

EXAMPLE 19

Tablets each weighing 0.150 g and containing 25 mg of the active substance, can be manufactured as follows:
Composition (for 10,000 tablets)

| | |
|---|---|
| 10β-(2-propynyl)-6-methylenestr-4-ene-3,17-dione | 250 g |
| Lactose | 800 g |
| Corn starch | 415 g |
| Talc powder | 30 g |
| Magnesium stearate | 5 g |

The 10β-(2-propynyl)-6-methylen estr-4-ene-3,17-dione, the lactose and half the corn starch are mixed; the mixture is then forced throught a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 20

Capsules, each dosed at 0.200 g and containing 20 mg of the active substance can be prepared as follows.
Composition for 500 capsules:

| | |
|---|---|
| 10β-(2-propynyl)-6α-azidoestr-4-ene-3,17-dione | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

EXAMPLE 21

Capsules, each dosed at 0.200 g and containing 20 mg of the active substance can be prepared as follows.
Composition for 500 capsules:

| | |
|---|---|
| 10β-(2-propynyl)-6-methylenestra-1,4-diene-3,17-dione | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (I)

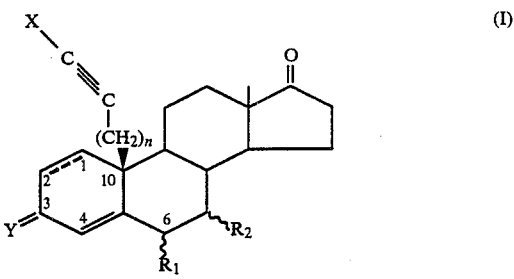

wherein
X is hydrogen, C$_1$–C$_4$ alkyl or halogen;
n is zero, 1 or 2;
Y is an oxo group or a methylene group;
the symbol ═══ indicates a single bond or a double bond;
R$_1$ is a C$_1$–C$_6$ alkylidene group; and
R$_2$ is hydrogen.

2. A compound of claim 1 wherein X is hydrogen, C$_1$–C$_4$ alkyl or halogen; n is zero, 1 or 2; Y is an oxo group; the symbol ═══ represents a single or a double bond; R$_1$ is C$_1$–C$_6$ alkylidene, and R$_2$ is hydrogen.

3. A compound of claim 1, wherein R$_1$ is methylidene.

4. A pharmaceutical composition containing a suitable carrier and/or diluent, and, as an active principle, an effective amount of the compound of claim 1 or a pharmaceutically acceptable salt thereof.

5. A method of producing an aromatose inhibiting effect in a patient in need of such inhibition, said method comprising administering to said patient an effective amount of a pharmaceutical composition of claim 4.

6. A method of inhibiting hormone-dependent tumors or prostatic hyperplasia in a patient in need of such inhibition, said method comprising administering to said patient an effective amount of the compound of claim 4.

7. A method of producing an aromatase inhibiting effect in a patient in need of such inhibition, said method comprising administering to the patient an effective amount of the compound of claim 1.

8. A method of inhibiting hormone-dependent tumors or prostatic hyperplasia in a patient in need of such inhibition, said method comprising administering to said patient an effective amount of the compound of claim 1.

9. A compound selected from the group consisting of:
10$\beta$-(2-propynyl)-6-methylenestra-1,4-diene-3,17-dione;
10$\beta$-(3-iodo-2-propynyl)-6-methylenestra-1,4-diene-3,17-dione;
10$\beta$-(3-bromo-2-propynyl)-6-methylenestra-1,4-diene-3,17-dione;
10$\beta$-(3-chloro-2-propynyl)-6-methylenestra-1,4-diene-3,17-dione;
10$\beta$-(3-fluoro-2-propynyl)-6-methylenestra-1,4-diene-3,17-dione;
10$\beta$-(2-propynyl)-6-methylenestr-4-ene-3,17-dione;
10$\beta$-(3-iodo-2-propynyl)-6-methylenestr-4-ene-3,17-dione;
10$\beta$-(3-bromo-2-propynyl)-6-methylenestr-4-ene-3,17-dione;
10$\beta$-(3-chloro-2-propynyl)-6-methylenestr-4-ene-3,17-dione; and
10$\beta$-(3-fluoro-2-propynyl)-6-methylenestr-4-ene-3,17-dione.

* * * * *